US00PP34263P2

(12) United States Plant Patent
Bradford et al.

(10) Patent No.: US PP34,263 P2
(45) Date of Patent: May 24, 2022

(54) NECTARINE TREE NAMED 'ROYAL PEARL'

(50) Latin Name: *Prunus persica*
Varietal Denomination: Royal Pearl

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 0 days.

(21) Appl. No.: 17/300,914

(22) Filed: Dec. 17, 2021

(51) Int. Cl.
*A01H 5/08* (2018.01)
*A01H 6/74* (2018.01)

(52) U.S. Cl.
USPC ..... Plt./188

(58) Field of Classification Search
USPC ..... Plt./187, 188
See application file for complete search history.

(56) References Cited

U.S. PATENT DOCUMENTS

| | | |
|---|---|---|
| PP15,845 P2 | 7/2005 | Bradford |
| PP19,919 P2 | 4/2009 | Bradford |
| PP22,758 P2 | 5/2012 | Bradford |

*Primary Examiner* — Susan McCormick Ewoldt

(57) ABSTRACT

The present invention relates to a new and distinct variety of nectarine tree, *Prunus persica*, broadly characterized by a large size, vigorous, hardy, self-fertile, productive and regular bearing tree. The variety blooms during the early season and requires about 400 chilling hours. The fruit matures under the ecological conditions described in the latter part of May, with first picking on May 17, 2021. The fruit is uniform, medium to large in size, sub-acidic and very sweet in flavor, globose to oblate in shape, semi-freestone in type, firm in texture, white in flesh color, and red with freckles in skin color.

1 Drawing Sheet

Botanical classification: *Prunus persica.*
Variety denomination: 'ROYAL PEARL'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of nectarine tree, which has been denominated varietally as 'Royal Pearl'.

In 2013 we made a first generaLion hybridization using 'Pearl Princess V' (U.S. Plant Pat. No. 19,919) peach as the selected seed parent and 'Rose Bright' (U.S. Plant Pat. No. 15,845) nectarine as the selected pollen parent. Upon reaching maturity the fruit of this hybridization was gathered, and the seeds were removed, cracked, stratified, germinated, and grown as seedlings on their own root in our greenhouse facility. Upon reaching dormancy we transplanted them to a cultivated area of our experimental orchard located near Le Grand, Calif., in Merced County (San Joaquin Valley). During the fruit evaluation season of 2017 we selected the present variety as a single tree from the group of seedlings described above. Subsequent to origination of the present variety of nectarine tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is similar to its seed parent, 'Pearl Princess V' (U.S. Plant Pat. No. 19,919) peach, by being self-fertile and by producing fruit that is white in flesh color, that is medium to large in size, and that is mostly red in skin color, but is quite distinguished from it by being a nectarine instead of a peach and by maturing about thirty days earlier.

The present variety is similar to its pollen parent, 'Rose Bright' (U.S. Plant Pat. No. 15,845) nectarine, by being self-fertile and by producing nectarines that are mostly red in skin color, that are firm in texture, and that mature in the early season, but is quite distinguished from it by producing fruit that is somewhat larger in size, white instead of yellow in flesh color, sub-acidic instead of acidic in flavor, and much sweeter in flavor.

The present variety is most similar to 'Pearlicious I' (U.S. Plant Pat. No. 22,758) nectarine by being self-fertile, by blooming in the early season, by having a large blossom, by having reniform leaf glands, and by producing nectarines that are white in flesh color, that are almost full red in skin color, that are firm in texture, and that are sweet and sub-acidic in flavor, but is distinguished therefrom by producing nectarines that are slightly larger in size, that are semi-freestone instead of clingstone in type, that have a bitter instead of sweet kernel, and that mature about nine days earlier.

SUMMARY OF VARIETY

In summary, the present nectarine variety is characterized by a large size, vigorous, hardy, self-fertile, productive and regular bearing tree. The variety blooms during the early season and requires about 350 chilling hours. The fruit matures under the ecological conditions described in the latter part of May, with first picking on May 17, 2021. The fruit is uniform, medium to large in size, sub-acidic and very sweet in flavor, globose to oblate in shape, semi-freestone in type, firm in texture, white in flesh color, and red with freckles in skin color.

DRAWING

The accompanying photograph consists of four whole fruits positioned to display the characteristics of the skin color and form, one divided fruit to reveal the flesh, a typical stone, typical leaves, a tip shoot of new leaf growth, and three insets depicting the flower buds and blossoms as they appear on the tree during the blooming season.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on May 23, 2021, on the original tree during its eighth growing season. The blossom and flower descriptions were made the previous blooming season. All major color code designations are by reference to the Inter-Society Color Council, National Bureau of Standards. Common color names are also used occasionally.

PARENTAGE

Seed parent: 'Pearl Princess V' (U.S. Plant Pat. No. 19,919) peach.

Pollen parent: 'Rose Bright' (U.S. Plant Pat. No. 15,845).

TREE

Size: Large, reaching and maintaining a height of 12' [3.66 m.] and a spread of 10' [3.05 m.] after eight growing seasons utilizing typical dormant pruning.

Vigor: Vigorous, responding about average to irrigation and fertilization. The variety grows about 3' [0.91 m.] of surplus top-growth during the spring and summer. The plant should be grown on a standard commercial rootstock for production purposes.

Growth: Spreading and dense.

Form: Pruned to a vase shape.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-fertile.

Bearing: Regular bearer, with no crop failures observed.

Chilling requirement: Relatively low, about 350 hours.

Leaf bud burst: Medium, during the middle of flowering.

Trunk:

- *Size.*—Stocky, reaching a maximum diameter of 6½" [165 mm.] after the eighth growing season.
- *Texture.*—Medium to shaggy.
- *Bark color.*—A Strong brown [55. s.Br] and Grayish brown [61. gy.Br] variegation with Dark brown [59. d.Br] crevices present.
- *Lenticels.*—Approximate Number Per Square Inch: 12. Color: Strong yellowish brown [74. s.yBr]. Average Size: ⅜" [9.5 mm.] in length. The width is typically one fourth as much as the length. Shape: Elongated.

Branches:

- *Size.*—Medium, diameter of main scaffold is 3" [76.2 mm.] measured 12" above the crotch, diameter of limb is 1½" [38.1 mm.] measured 12" above the first fork.
- *Texture.*—Smooth to medium on first and second year wood, increasing in roughness with age.
- *Color.*—1st Year Wood Topside: Grayish red [19. gy.R]. 1st Year Wood Underside: Brilliant yellow green [116. brill.YG]. Older Wood: A Light grayish brown [60. l.gy.Br] and Grayish brown [61. gy.Br] variegation with Dark grayish brown [62. d.gy.Br] crevices present.
- *Lenticels.*—Number Per Square Inch: About 45 on second year wood. Color: Deep orange yellow [69. deep OY]. Average Size: Medium, 1/16" [1.6 mm.] in length. The width is typically one fourth as much as the length. Shape: Elongated.

Leaves:

- *Size.*—Large. Average Length: 6" [152.4 mm.]. Average Width: 1¾" [44.5 mm.].
- *Arrangement.*—Alternate.
- *Thickness.*—Medium.
- *Form.*—Elliptical.
- *Apex.*—Acuminate.
- *Base.*—Rounded to acute with an average base angle of 75 degrees.
- *Surface.*—Smooth on both sides.
- *Color.*—Dorsal Surface: Moderate olive green [125. m.OlG]. Ventral Surface: Moderate yellow green [120. m.YG].
- *Red midvein.*—Absent.
- *Margin.*—Finely serrate.
- *Venation.*—Pinnately net veined.
- *Petiole.*—Average Length: 5/16" [7.9 mm.]. Average Thickness: 1/16" [1.6 mm.]. Color: Strong yellow green [117. s.YG].
- *Stipules.*—Number: 2 per leaf, up to 6 per growing tip. Average Length: ¼" [6.4 mm.]. Color: Vivid yellow green [115. v.YG] becoming Moderate brown [58. m.Br] with age.
- *Glands.*—Number: 2 to 4 per leaf. Position: Alternate, first pair is located at the intersection of petiole and base of blade. Form: Reniform. Size: Medium, about 1/32" [0.8 mm.] in diameter. Color: Light yellow green [119. l.YG] becoming Moderate brown [58. m.Br] with age.
- *Leaf buds.*—Pointed.

Flower buds:

- *Hardiness.*—Hardy, with respect to central California blooming season.
- *Diameter.*—Typically ⅜" [9.5 mm.] 1 week before bloom.
- *Length.*—Typically ⅝" [15.9 mm.] 1 week before bloom.
- *Form.*—Not appressed.
- *Surface.*—Pubescent.
- *Tip color.*—Pale purplish pink [252. p.pPk].

Flowers: Perfect, complete, perigynous, usually a single pistil, about thirty stamens, five sepal and petal locations alternately positioned.

*Type.*—Showy, large.
*Average flower diameter.*—1 13/16" [46.0 mm.].
*Average flower depth.*—½" [12.7 mm.] when fully open.
*Number of petals.*—Five, extra petal fragments occasionally observed, double blossoms not observed.
*Petal arrangement.*—Overlapping.
*Petal shape.*—Circular to oval.
*Petal margin.*—Entire, slightly wavy.
*Average petal diameter.*—13/16" [20.6 mm.].
*Average petal length.*—13/16" [20.6 mm.].
*Petal apex.*—Rounded.
*Petal base.*—Rounded to very slightly cordate.
*Petal color.*—Light pink [4. l.Pk] toward the apex and Moderate pink [5. m.Pk] toward the base on both sides.
*Anthocyanin coloration intensity.*—Weak.
*Anther color.*—Moderate red [15. m.R] surrounding a Light yellow [86. l.Y] center at bloom onset.
*Pollen.*—Anthers produce an abundance of Brilliant yellow [83. brill.Y] pollen.
*Stigma color.*—Light greenish yellow [101. l.gY].
*Stigma position.*—Typically located slightly above the nearby anthers.
*Stamen position.*—Typically located about 1/16" [1.6 mm] below the petals.
*Average pistil length.*—¾" [19.1 mm.].
*Average stamen length.*—9/16" [14.3 mm.].
*Ovary.*—Non-pubescent.
*Sepal color.*—Grayish purplish red [262. gy.pR] on the outer surface. The inner surface is a somewhat translucent Pinkish white [9. pkWhite] with both Grayish purplish red [262. gy.pR] and Vivid yellow green [115. v.YG] areas visible.
*Sepal length.*—⅜" [9.5 mm.].
*Sepal width.*—¼" [6.4 mm.].
*Sepal apex.*—Rounded to elliptical to match the sepal length and width.
*Sepal margin.*—Fairly smooth.
*Sepal outer surface.*—Pubescent.
*Fragrance.*—Moderate.
*Blooming period.*—Early, blooms about four days before 'May Bright' (U.S. Plant Pat. No. 21,928) nectarine.
*Onset of bloom.*—One percent on Feb. 8, 2021.
*Date of full bloom.*—Feb. 20, 2021.
*Duration of bloom.*—One to two weeks, dependent on ambient temperature.
*Bloom density.*—Medium to heavy.
*Number per cluster.*—1 to 3 with single flowers most common.

FRUIT

Maturity when described: Shipping ripe, May 23, 2021.
Date of first picking: May 17, 2021.
Date of last picking: May 28, 2021.
Size: Uniform, medium to large.
*Average diameter axially.*—2¾" [69.9 mm.].
*Average diameter across suture plane.*—3" [76.2 mm.].
*Average diameter across cheek plane.*—3" [76.2 mm.].
*Typical weight.*—7.9 ounces [224 grams].
Form: Uniform, globose to oblate, symmetrical.
*Longitudinal section form.*—Oblate.
*Axial view.*—Round.
Suture: A shallow trough extending from the base, continuing along the side, and becoming a shallow groove that ends with a slight depression just beyond the pistil point.
*Near the base.*—A shallow trough.
*Along the side.*—A shallow trough.
*Near the apex.*—A shallow groove.
Ventral surface: Rounded, slightly lipped toward the apex on both sides.
Lips: Slightly unequal.
Cavity: Flaring, circular, suture showing on one side, Pale greenish yellow [104. p.gY] stem markings present.
*Depth.*—½" [12.7 mm.].
*Breadth.*—1¼" [31.8 mm.].
Base: Truncate.
Apex: Rounded, somewhat cordate when viewed parallel to the suture.
Pistil point: Apical, negligible in length, Light yellow [86. y.Y] on the tip, depressed within the suture.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to the flesh.
*Astringency.*—Non-astringent.
*Tendency to crack.*—None observed.
*Color.*—Very deep red [14. v.deep R] over a Moderate red [15. m.R] background with moderate Pale yellow [89. p.Y] freckling stronger toward the apex.
Flesh:
*Color.*—Yellowish white [92. yWhite] with almost no red streaking or flecking.
*Surface of pit cavity.*—Covered in Pale yellow [89. p.Y] broken fibers when twisted away from the stone.
*Amygdalin.*—Scarce.
*Juice.*—Abundant, rich.
*Texture.*—Firm, tough.
*Fibers.*—Abundant, fine, tender.
*Ripens.*—Fairly even, slightly earlier at the shoulders.
*Flavor.*—Sub-acidic, a tasty blend of high sugar and low acid, typically 20 brix.
*Aroma.*—Moderate.
*Eating quality.*—Excellent.

STONE

Type: Semi-freestone.
Form: Oval.
Hilum: Narrow, oblong.
Base: Rounded.
Apex: Rounded with a protruding tip.
Sides: Equal.
Tip: Sharp, 1/16" [1.6 mm.] in length.
Surface: Irregularly furrowed toward the apex, pitted toward the base.
Ridges: Jagged.
External color: Light yellowish brown [76. l.yBr] when first removed.
Pit wall color when cracked: Pale orange yellow [73. p.OY].
Cavity surface color: A Dark orange yellow [72. d.OY] and Deep yellowish brown [75. deep yBr] two-tone.
Average pit wall thickness: ¼" [6.4 mm.].
Average length: 1¼" [31.8 mm.].
Average width: 1 1/16" [27.0 mm.].

Average breadth: 13/16" [20.6 mm.].
Tendency to split: None observed.
Kernel:
*Form.*—Oval.
*Skin color.*—Pale yellow [89. p.Y].
*Pellicle color.*—Dark olive brown [96. d.OlBr].
*Vein color.*—Light yellow [86. l.Y].
*Taste.*—Bitter.
*Viable.*—Yes.
*Average length.*—¾" [19.1 mm.].
*Average width.*—½" [12.7 mm.].
*Amygdalin.*—Abundant.

USE

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: Not tested.
Resistance to diseases: Not tested.

OTHER NOTES

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, that is most similar to 'Pearlicious I' (U.S. Plant Pat. No. 22,758) nectarine by being self-fertile, by blooming in the early season, by having a large blossom, by having reniform leaf glands, and by producing nectarines that are white in flesh color, that are almost full red in skin color, that are firm in texture, and that are sweet and sub-acidic in flavor, but is distinguished therefrom by producing nectarines that are slightly larger in size, that are semi-freestone instead of clingstone in type, that have a sweet instead of bitter kernel, and that mature about nine days earlier.

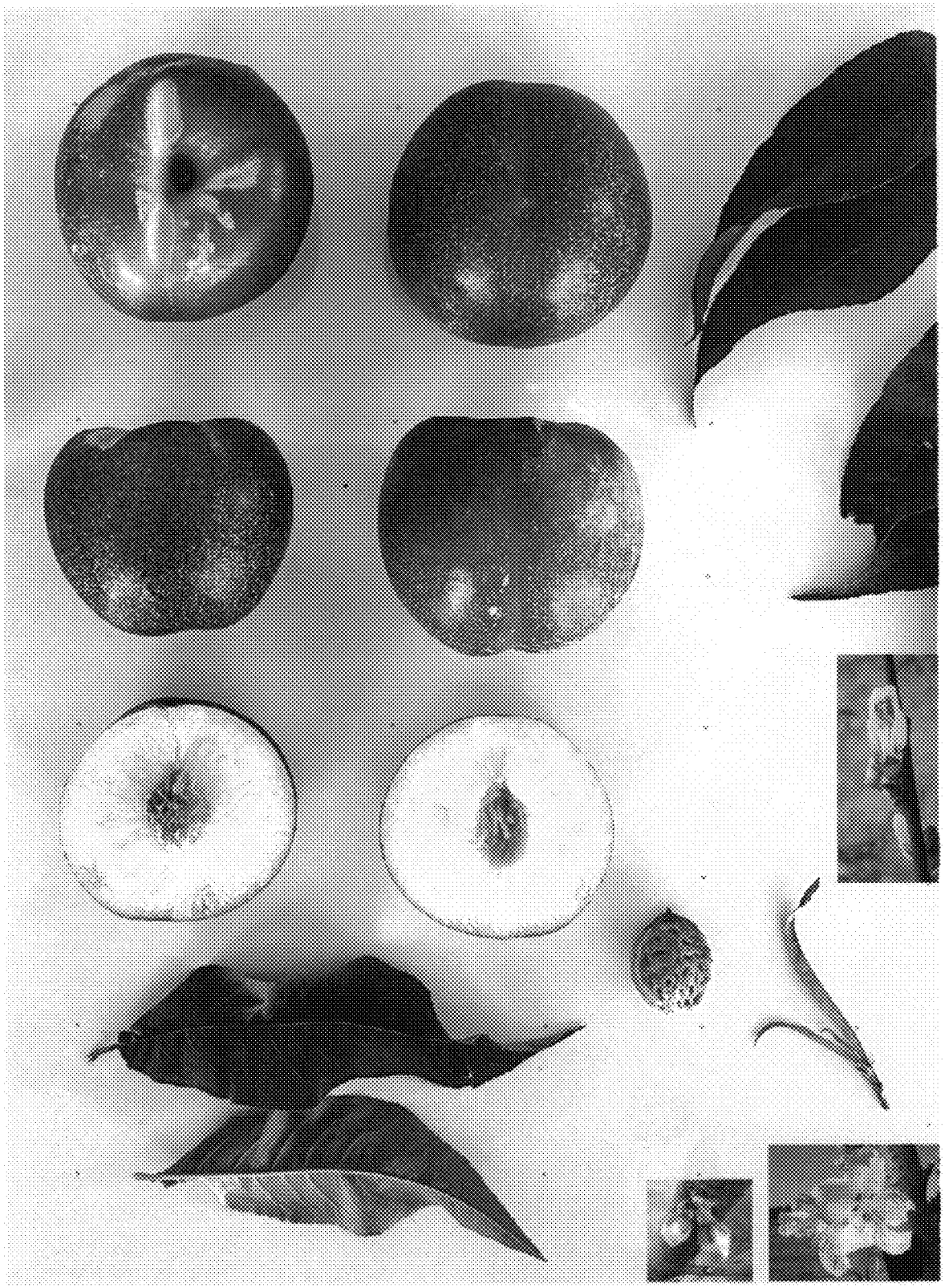

* * * * *